(12) United States Patent
Hasegawa et al.

(10) Patent No.: US 9,139,907 B2
(45) Date of Patent: Sep. 22, 2015

(54) METHOD FOR PRODUCING METAL COMPLEX QUANTUM CRYSTALS

(75) Inventors: Yuki Hasegawa, Himeji (JP); Katsuyuki Hasegawa, Himeji (JP)

(73) Assignee: MYTECH CO., LTD, Himeji-shi, Hyogo (JP)

( * ) Notice: Subject to any disclaimer, the term of this patent is extended or adjusted under 35 U.S.C. 154(b) by 154 days.

(21) Appl. No.: 13/821,235

(22) PCT Filed: Sep. 6, 2011

(86) PCT No.: PCT/JP2011/070274
§ 371 (c)(1),
(2), (4) Date: May 20, 2013

(87) PCT Pub. No.: WO2012/033097
PCT Pub. Date: Mar. 15, 2012

(65) Prior Publication Data
US 2013/0230660 A1 Sep. 5, 2013

(30) Foreign Application Priority Data

Sep. 6, 2010 (JP) ................................. 2010-198555

(51) Int. Cl.
*B82B 3/00* (2006.01)
*B82Y 15/00* (2011.01)
(Continued)

(52) U.S. Cl.
CPC ................. *C23C 16/50* (2013.01); *C01B 17/64* (2013.01); *C01G 5/00* (2013.01); *G01N 21/658* (2013.01); *C01P 2002/82* (2013.01); *C01P 2004/03* (2013.01); *C01P 2004/04* (2013.01); *C01P 2004/24* (2013.01); *C01P 2004/61* (2013.01)

(58) Field of Classification Search
USPC ........................................................... 205/85
See application file for complete search history.

(56) References Cited

U.S. PATENT DOCUMENTS

| 5,607,643 A | 3/1997 | Xiaoming et al. |
| 2008/0286526 A1 | 11/2008 | Konakahara |
| 2010/0149530 A1 | 6/2010 | Tomaru |

FOREIGN PATENT DOCUMENTS

| JP | 07-146295 A | 6/1995 |
| JP | 11-61209 A | 3/1999 |

(Continued)

OTHER PUBLICATIONS

Shon, "Monolayer-Protected Bimetal Cluster Synthesis by Core Metal Galvanic Exchange Reaction", Langmuir, vol. 18, (2002), pp. 3880-3885.*

(Continued)

*Primary Examiner* — Lisha Jiang (57) ABSTRACT

The present quantum crystals are produced by a method characterized in that an aqueous solution of plasmon metal complex made from a ligand and a plasmon metal selected from the group consisting of gold, silver, copper, nickel, zinc, aluminum, and platinum is prepared and brought into contact with a carrier made of a metal or a metal alloy having an electrode potential lower than an electrode potential of the plasmon metal in the aqueous solution. When the plasmon metal complex is precipitated as quantum crystals arranged on the carrier, the metal complex crystals are formed as metal quantum dots.

10 Claims, 9 Drawing Sheets

(51) Int. Cl.
*B82Y 30/00* (2011.01)
*B82Y 40/00* (2011.01)
*C23C 16/50* (2006.01)
*G01N 21/65* (2006.01)
*C01B 17/64* (2006.01)
*C01G 5/00* (2006.01)

(56) References Cited

FOREIGN PATENT DOCUMENTS

| | | | |
|---|---|---|---|
| JP | 2006-083450 A | 3/2006 | |
| JP | 2007-198933 A | 8/2007 | |
| JP | 2008-281529 A | 11/2008 | |
| JP | 2010-203973 A | 9/2010 | |
| WO | 2008/010442 A1 | 1/2008 | |

OTHER PUBLICATIONS

Lai et al., "Silver Nanoplates Prepared by Modified Galvanic Displacement for Surface-Enhanced Raman Spectroscopy", Nanoscale, vol. 3, (Mar. 2011), pp. 2134-2137.*
International Search Report directed to PCT/JP2011/070274, 5 pages including English translation.
Shuming Nie et al., Probing Single Molecules and Single Nanoparticies by Surface-Enhanced Raman Scattering; Science 275, 1102 (1997); DOI:10.1126/science.275.5303.1102, total 6 pages.
Katherine C. Grabar et al., Kinetic Control of Interparticle Spacing in Au Colloid-Based Surfaces: Rational Nanometer-Scale Architecture, J. Am. Chem. Soc., vol. 118, No. 5, 1996, pp. 1148-1153.
Robin M Bright et al., Preparation and Characterization of Ag Colloid Monolayers; Langmuir, vol. 14, No. 20, 1998, p. 5695-5701.

* cited by examiner

METHOD FOR PRODUCING METAL COMPLEX QUANTUM CRYSTALS

CROSS-REFERENCE TO RELATED APPLICATION

This application claims priority to and is a continuation of PCT Application No. PCT/JP2011/070274, filed Sep. 6, 2011, the entire contents of which are incorporated herein by reference.

TECHNICAL FIELD

The present invention relates to a method of producing a quantum crystal of metal complex including metal nanoclusters or nanoclusters as metal quantum dots by using an aqueous solution of the metal complex and its use based on the effect of localized surface plasmon enhancement.

BACKGROUND OF THE INVENTION

Field of the Invention

As a typical material of the next generation in the nano technology, surface modified nano particles, which are made from metal atoms by controlling a shape and a size in nano level so as to form a nanocluster or nanoclusters, have been drawing attention, because nanoclusters can be designed to have a new electronic property or materiality due to so-called quantum size effect which would happen in nanometer area. Hereinafter, the word "nanocluster" means agglomeration of several to several hundred atoms and molecules having several nm (nano meters) to several 10 nm in size. It is known that these clusters are bigger than a single molecule, and smaller than a nano crystal. The nanocluster is a material which shows a unique function or property different from that in a state of atoms, molecules and bulk crystals. Therefore, by controlling the size and the number of material composition atom, a new knowledge and a finding concerning a phase transition, a crystal growth, a chemical reaction, catalytic action, and the like are expected. One of them is a so-called Surface Plasmon Resonance (SPR) on the metal surface. In general, electrons in the metal do not tend to interact with light, but the light can interact with electrons existing in metal nano particles under a special condition, resulting in occurrence of so called Localized Surface Plasmon Resonance. Especially, according to the theoretical consideration of so-called "dimmer of nano Ag particles" in case in which the silver nano particles are positioned in a predetermined distance, it is thought that the degree of electric field enhancement made by the wavelength around 400 nm-would be particularly very high, and in case of less than 400 nm, there would exist a peak at the wavelength around 300 nm. And, in relation to the particles diameter, it is thought that as a particle diameter is widened, the position of the peak becomes high, and further, the peak would shift to the long wave side and the peak width would become bigger, so that the field enhancement effect can be expected in a wide range of wavelength.

Therefore, it has been proposed that on a substrate for measuring SERS (Surface Enhance Raman Scattering), in order to accumulate nano particles of Noble metal such as Ag, Au and the like having a diameter of about several 10 nm, there have been used a Chemical Vapor Deposition (CVD) method or a method for synthesizing colloidal particles of Ag or Au in an aqueous solution and fixing it on a glass substrate which is decollated by lysine or cyan (referring to the following Non-patent literatures 1 to 3 and Patent Document 1). Therefore, at the present, the above CVD method has now to be used for mass-production of the SERS substrate.

RELATED ART DOCUMENT

Patent Document

Patent Document 1: Japanese Patent Application Laid-Open Publication No. 11(1999)-61209

Non-Patent Literatures

Non-patent Literature 1: S. Nie and S. R. Emory, Science. 275, 1102 (1997)
Non-patent Literature 2: K. C. Grabar, P. C. Smith, M. D. Musick, J. A. Davis, D. G. Walter, M. A. Jackson, A. P. Guthrie and M. J. Natan, J. Am. Chem, Soc., 118, 1148 (1996)
Non-patent Literature 3: R. M. Bright, M. D. Musick and M. H. Natan, Langmuir, 14, 5695 (1998)

SUMMARY OF THE INVENTION

Problems to be Solved by the Invention

However, the substrate formed by the CVD method does not have a function for absorbing a sample to be detected, so that the substrate for SERS detecting has to be prepared by so-called drop & dry method including coating and drying steps of the sample to be detected. It is difficult for the prompt detection and therefore, it has a disadvantage due to the deterioration of the sample. Furthermore, there is the biggest disadvantage in the matter of a poor repeatability of the measurement, resulting in a great problem of barrier for variety applications of the SERS method.

Therefore, the inventors came back to the fundamental points of the SERS function and/or phenomenon and deeply thought it to overcome the above problems. It is known that the degree of enhancement in the surface plasmon phenomenon is depended on a variety of physical and chemical parameters including various atom bonding position and orientation existing in absorbed molecules on the electro-magnetic field of the metal surface. Accordingly, in order to provide a best substrate for keeping a good repeatability in relation of the SERS measuring, it is necessary to develop the substrate from the following two points relating to the mechanism of the occurrence of the SERS; (i) achievement of the best physical condition for surface plasmon resonance in the metal to enhance a local strength of the incident light and (ii) achievement of the best chemical condition for formation of so-called charge-transfer complex between metal surfaces and Raman active molecules to be absorbed and transition thereafter. The inventors have found that in order to achieve the best physical condition, it is possible to apply the CVD method as long as the physical condition is concerned, although it is difficult to control the particle size and orientation. However, at the same time, it is impossible for the CVD method to achieve the best chemical condition for the formation of the charge-transfer complex.

By the way, in recent years, it has been reported that Prof. Kimura, Ph.D. of Hyogo prefectural university succeeded in the preparation of a two or three dimensional artificial particle crystal by using nano particles as component or element for the crystal, and further succeeded in the IV group cluster crystal from the aqueous solution by using the Si cluster. It is the first successful case in the world. The crystal of these particles can be said as the quantum dot crystal which has the periodic structure of nanometer, and it has come to be expected as the key material of the nano-technology in the 21st century. Taking about the above findings and knowledge into consideration, in order to provide a new method for making a crystal of metal quantum dots on the substrate in place of the prior CVD method, the inventors have made a lot of research by using a various kinds of metal complex in the aqueous solution and have found that in case in which a plasmon metal can coordinate with a ligand and form a metal complex in the aqueous solution, the metal complex tends to crystalize into quantum crystals on a metal substrate and metal nanoclusters included in the quantum crystals are formed as quantum dots, resulting in observation of strong plasmon enhancement effect which has never been seen before. It would be caused by a function due to the formation of charge-transfer complex.

Means for Solved by the Invention

The present invention relates to a method of producing quantum crystals of metal complex and has been made on the basis of the above new knowledge, which includes a step of providing a plasmon metal complex aqueous solution including a ligand and a plasmon metal selected from the group consisting of Au, Ag, Cu, Ni, Zn, Al and Pt, a step of contacting the aqueous solution of the plasmon metal complex with a carrier made of a metal or a metal alloy showing an electrode potential lower (ionization tendency higher) than an electrode potential of the plasmon metal or a carrier made of metal being adjusted at an electrode potential lower than the electrode potential of plasmon metal in the aqueous solution, and a step of depositing the plasmon metal complex from the aqueous solution on the carrier to form and arrange the quantum crystals having plasmon enhancement effect on the carrier.

It is remarkable that the deposition and agglomeration of plasmon metal complex from the aqueous solution on the metal carrier is effective on production of the conditions relating to mechanism of SERS phenomenon, one of which is the achievement of (i) the best physical condition for surface plasmon resonance enhancing the local strength of incident light and (ii) the best chemical condition for formation of the charge-transfer complex between the metal surface and Raman active molecules.

Figure 7:
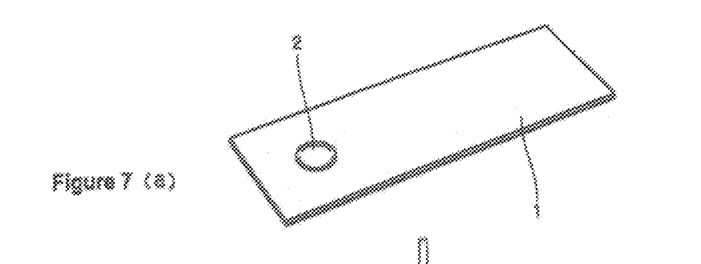
FIG. 7 is a drawing showing a process for preparing a SERS substrate.
Figure 8:
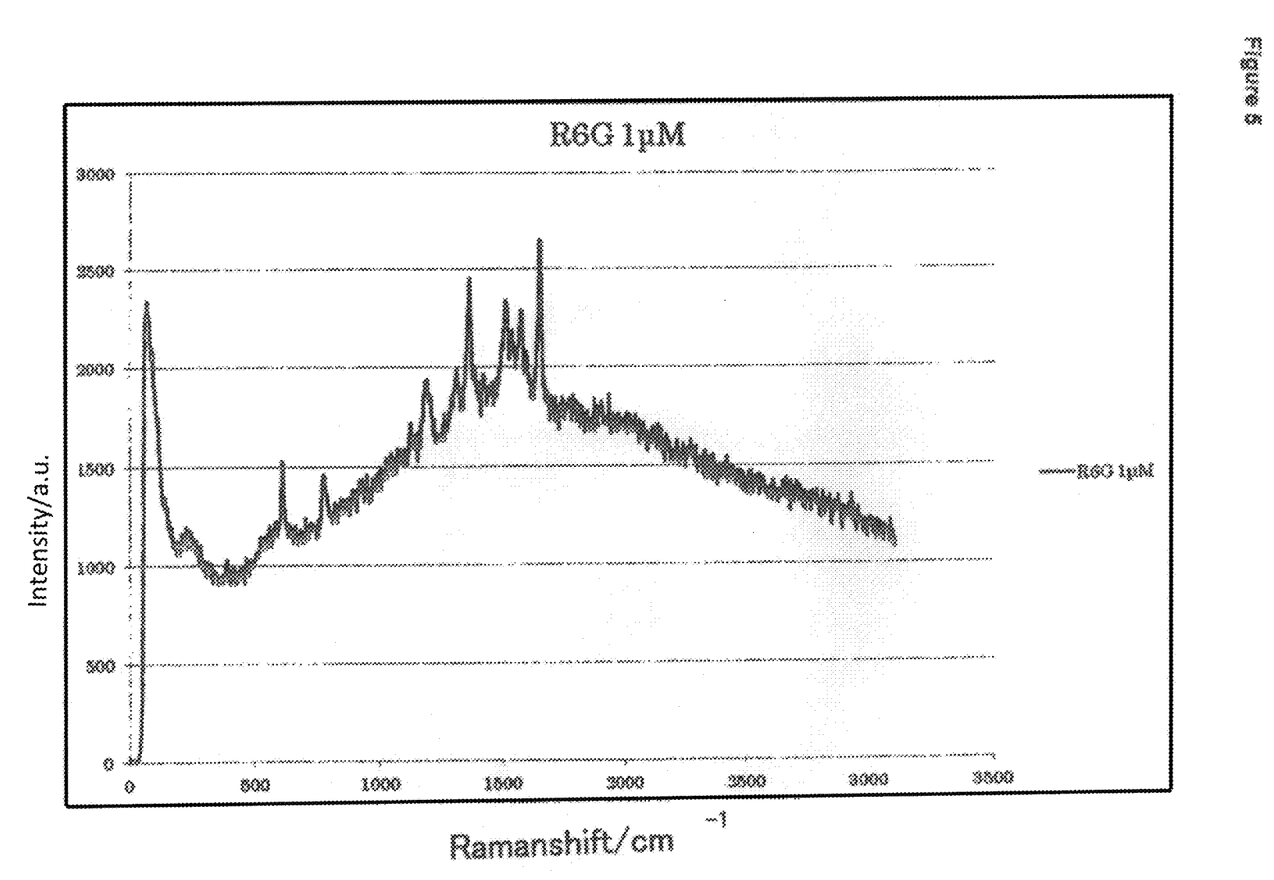

As a carrier which forms the quantum crystal, one of the group consisting of a metal particle, a metal needle, and a metal film inside the capillary may be chosen corresponding to the use of metal quantum crystal. For example, in case of silver plasmon metal, the metal carrier is chosen in order to have an electrode potential lower (ionization tendency higher) than that of Ag plasmon metal or complex to be deposited on the metal carrier. For example, the carrier made of metal may be selected from the group consisting of copper, brass and phosphor bronze, and the form of the carrier is adopted so as to receive a drop of the metal complex solution as shown in FIG. 7, on which the aqueous solution of sample to be measured is put a drop on the prepared carrier and then SERS detection may be done. In case of the metal particles provided with quantum crystals of the plasmon metal complex, it can be used for a light transmission electrode material used in the light-incident side of the solar battery. In case of a metal needle provided with quantum crystals of the plasmon metal complex, it can be used for the thermal therapy, wherein the metal needle is inserted into the affected part directly, and the quantum crystal part becomes hot due to surface enhancement resonance by the laser irradiation. In case of a capillary including quantum crystals of the plasmon metal complex, the small sample is absorbed therein without being contaminated. Therefore, the quantum crystals of the present invention can be formed on the metal film or a piece of metal made by chemical deposition or metal parts inserted in the capillary.

Figure 2:
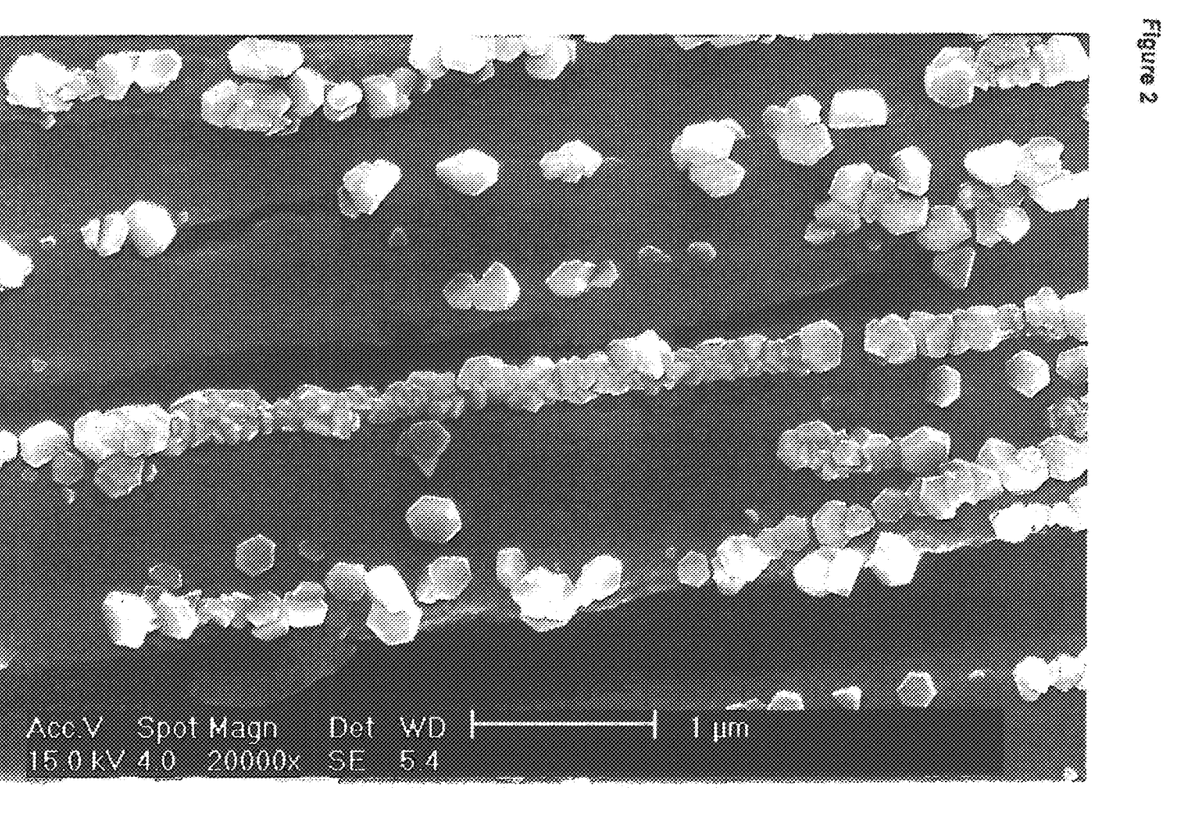
FIG. 2 is a photograph (20,000 times) of scanning type electron microscope, which shows a state of formation that the silver complex crystal forms a hexagonal plate-like crystal on the brass substrate.

The metal complex is formed in the manner in which the quantum crystal of the present invention includes nanocluster of plasmon metal particles on the metal carrier (refer to FIGS. 2, 3(a) and 3(b)). From the effect of strong plasmon enhancement on the surface of plasmon metal, it presumes that the plasmon metal particles are agglomerated in a state of nanoclusters having average size of several nano meters to ten and several nano meters so that quantum dots having nano size are formed with an arrangement at certain regular intervals. As a result, the best physical condition for the aspect of (i) the surface plasmon resonance enhancing local strength of the incident light can be provided.

Further, as the metal complex is crystallized on the metal carrier, it can presume that at least a part of plasmon metal particles to form nanocluster is deposited in a state of metal and also a remainder of plasmon metal particles is deposited in a state of a metal complex ion bonding with the ligand, so that plasmon metal complexes can keep or make an ionized state which can absorb a sample to be detected by drop of the solution so that (ii) plasmon metal particles and Raman active molecules make a charge-transfer complex. As a result, SERS detection can be instantly applied in a state of solution of the sample without drying before detection.

The plasmon metal in the present invention can coordinate with a various kinds of ligands so as to deposit metal complexes from the aqueous solution on the metal substrate. The ligand to be chosen for the metal complexes should be determined by considering important parameters relating to the formation of the quantum crystal of metal complexes such as a constant of the metal complex stability in the aqueous solution, a complex structure coordinated with ligands and the like. It is important that at least the selection of ligands should be done by considering that the metal complex to be formed between the plasmon metal and the ligand becomes a complex for forming a charge-transfer complex with the sample. At the present, a ligand selected from the group consisting of an amino acid ion, an ammonia ion, a thiosulfate ion and a nitrate ion, can form the plasmon metal complexes and coordinate with the plasmon metal quantum dots as a ligand, which surface plasmon resonance can be detected by the SERS method. As a result, it presumes that (i) the best physical condition for surface plasmon resonance enhancing local strength of incident light and (ii) the best chemical condition for formation of the charge-transfer complex between the metal surface and Raman active molecules and transition thereafter can be achieved by formation of the quantum crystal of the plasmon metal complexes, so that it comes to know that the in order to detect the sample by SERS method, it is preferable to ion-bond with plasmon metal particles by electro-charge.

When the above plasmon metal complex is formed according to the present invention, it is preferable that one selected from the group consisting of Au (gold), Ag (silver) and Cu (copper) is chosen as the plasmon metal.

The metal concentration in the aqueous solution of the plasmon metal complex is 500 to 5,000 ppm, and the concentration of 500 to 2,000 ppm is particularly preferable. In case in which Ag plasmon metal is used, a determined amount of silver chloride is added into the aqueous solution including a ligand compound such as ammonia and a sodium thiosulfate to make silver complex with the ligand. The aqueous solution in the present invention is used for making the metal complex to be precipitated and agglomerated on the metal carrier in order to produce nano metal dots arranged in a suitable intervals on the metal carrier. In case of less than 500 ppm, it is impossible to form nano metal dots in the suitable intervals or it needs a long time to make nano metal dots in the suitable intervals. On the other hand, in case of more than 2,000 ppm, it is difficult to control the dots in suitable intervals due to the prompt deposition and agglomerate of the metal complex. The preservation of the metal complex solution can be improved when a dispersant is added in order to prevent the metal complex or its ion from progress of agglomeration in the aqueous solution as long as a measurement is not obstructed.

In case of Ag nanocluster (cluster of 10-20 nm includes from twenty to forty Ag atoms), the dispersant may be added at 1/50 to 1/150 molar rate based on a weight of Ag atom. It can get a good localized plasmon enhancing effect with a silver thiosulfate complex, a silver amine complex, a silver nitrate complex and a silver amino acid complex in a range of Ag equivalent of 500 to 2000 ppm.

Figure 6:
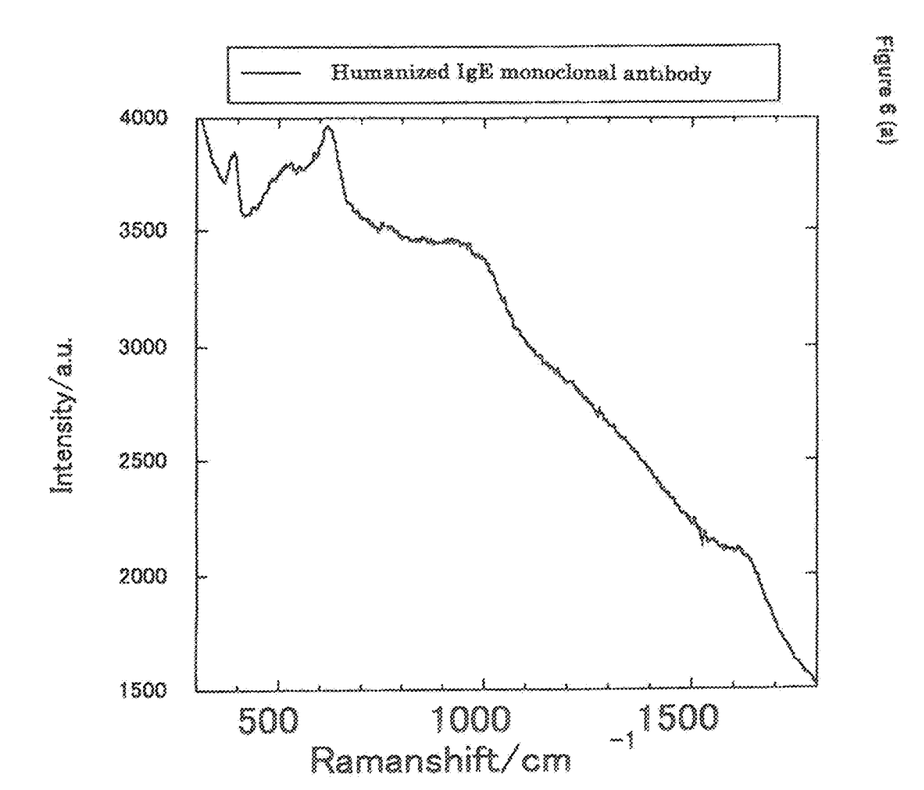
FIG. 6(a) is a graph showing a Raman scattering spectrum of antibody formed on phosphor bronze substrate prepared by antibody added aqueous solution of Ag thiosulfate according to the method of the present invention.
FIG. 6(b) is a graph showing a Raman scattering spectrum of antigen-antibody on phosphor bronze substrate prepared by a drop of antigen on the substrate of FIG. 6(a).

In the present invention, an antibody can be absorbed on the plasmon metal dots through an electro-charge therebetween as a ligand or a substitute of ligand, so that the antigen-antibody reaction can be detected by using the method of the present invention (referring to FIGS. 6 (a) and (b)).

Effects of the Invention

1) If the metal complex in the aqueous solution can be made of a various kinds of ligands and the plasmon metal to be coordinated with the ligand, the metal complex in the aqueous solution can be reductively deposited on the metal carrier by potential difference between the metal complex and the metal carrier to make the metal complex crystallized so as to form metal nanoclusters, which are included in quantum crystals, with the metal complex having a suitable quantum size and formed in a controlled arrangement which is the best physical condition resulting in achievement of a desirable quantum size effect. Among them, the nanoclusters of Au, Ag and Cu tend to form quantum dots which are useful materials for surface plasmon resonance excitation element.

2) Moreover, the metal complex leads to a good result of the repeatability in the SERS detection method, because it may be in the condition (ii) that a metal element of the metal complex is easy to be ionized and absorb the Raman activated molecule on the ionized surface of the metal or metal complex to form a charge-transfer complex which is the best chemical condition.

3) The metal complex is easy to control a charge property into a plus or minus which is easy to absorb a protein such as virus and the like. For example, if quantum dots of the metal complex are bonded with a protein Avidin or a living body material Biotin and deposited on the metal substrate, a SERS substrate suitable for the protein detection can be provided.

4) The metal complex is also possible to be bonded with an antibody in the aqueous solution by adding the antibody thereinto and dispersing it in the aqueous solution. Therefore, if the metal complex together with the antibody is deposited on the metal substrate, the choice of the antibody can provide a suitable substrate for absorbing a predetermined antigen and detecting the antigen in the antigen-antibody reaction.

5) If the metal complex is formed in the point of a metal needle, which can be inserted into the affected part directly, the plasmon enhancement effect is obtained by irradiation of the laser light, so that the needle point becomes hot and a hyperthermia therapy can be enforced in the affected part.

Figure 3:
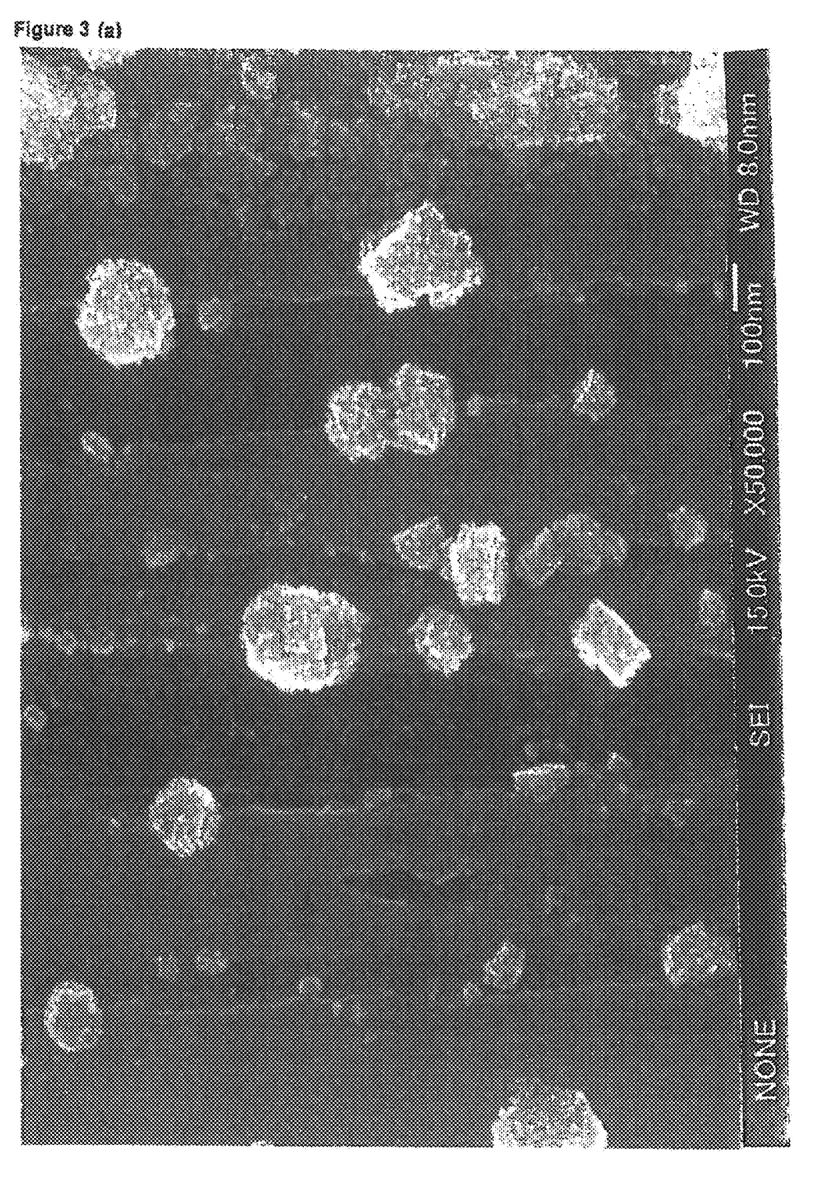
FIG. 3(a) is a photograph (50,000 times) of scanning type electron microscope, which shows a state of formation that the silver complex crystal forms quantum dots on the phosphor bronze substrate.
FIG. 3(b) is a photograph (200,000 times) of scanning type electron microscope-which shows the state that the silver complex crystal forms quantum dots crystal on the phosphor bronze substrate.

It is observed that the plasmon metal complex made of a silver coordinated with thiosulfate ion produces plate-like crystals of 100 to 200 nm on the metal substrate, which shows the excellent effects of surface plasmon resonance excitation and electro-field reinforcement, which may be probably resulted from the formation of quantum dots made by Ag nanocluster in the hexagonal plate-like crystals (as shown in FIGS. 3 (a) and (b)).

BRIEF DESCRIPTION OF THE DRAWINGS

FIG. 5 is a graph showing a Raman scattering spectrum of rhodamine 6G of 1 µM on a phosphor bronze substrate where Ag complex is formed in Ag thiosulfate aqueous solution according to the method of the present invention.

DETAILED DESCRIPTION OF THE INVENTION

The preferred embodiment of this invention is explained with reference to the following drawings in detail. As shown in FIGS. 7(a) to (c), a circle dish shaped metal plate 2 having a thickness of about 0.1 mm made by means of punching is adhered on a plate 1 made of glass or plastics. The substrate is provided with the circle dish shaped metal plate 2 so as to receive drops of the aqueous solution and there is a rise of the droplet 3 on the metal plate as shown in FIG. 7 (b). Thereafter, the droplet is blown out by a blow of Nitrogen gas and as a result, there is left an agglomeration area 4 formed on the surface of metal plate, where nanoclusters are formed as the quantum dots as shown in FIG. 7(c). In place of the thin metal plate 2, a metal film may be formed by a chemical plating or a chemical vapor deposition.

Example 1

Figure 1:
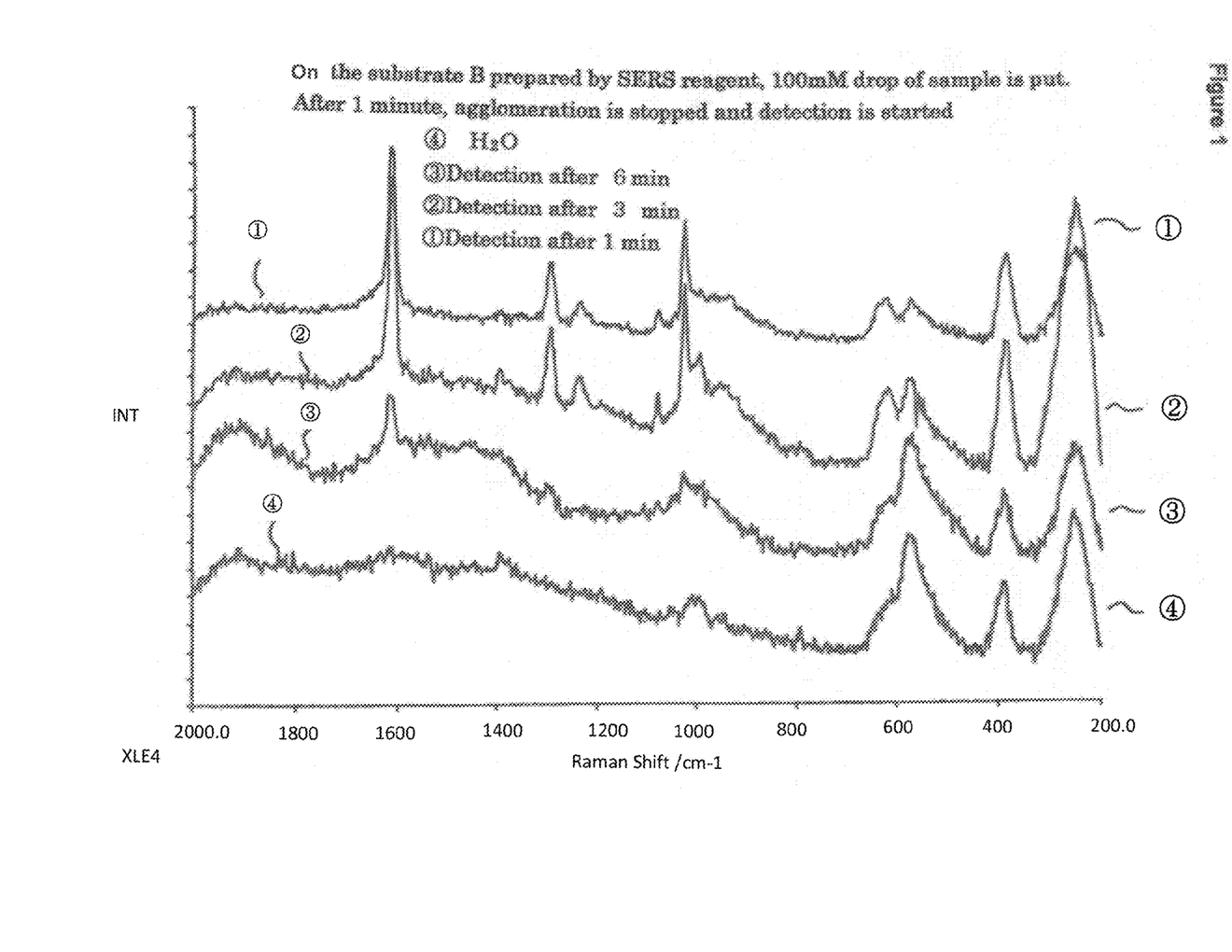
FIG. 1 is a graph showing a Raman scattering spectrum of 4,4'-bipyridine of 100 nM on a SERS substrate prepared according to the method of the present invention, from which an excellent plasmon resonance excitation effect is observed.

The aqueous solution of plasmon metal complex was prepared in the manner in which a predetermined amount of silver chloride was dissolved in an aqueous solution of sodium thiosulfate according to a known standard method. The aqueous solution was diluted with pure water up to a concentration of 500 to 2000 ppm (based on a weight of Ag atom), and amino acid (L-alanine) of 10 to 20 ppm was added to have a colorless solution containing Ag nanoclusters (Ag complex). One droplet (10 μL) of the metal complex aqueous solution was put on the brass substrate (Cu 60; Sn 40) and 3 minute later the droplet on the metal substrate was blown off and dried out to have a Surface Plasmon Resonance Excitation (SERS) substrate. FIG. 2 is a photograph of the scanning type electron microscope (20,000 times) of the surface profile of the SERS substrate. From the profile as shown in FIG. 2, it was confirmed that a hexagonal plate-like crystal of 100 to 150 nm was formed on the substrate. In case of Ag complex crystals formed on the phosphor bronze substrate, the photographs (50,000 and 200,000 times) of the scanning type electron microscope show formation of a lot of nano metal dots encapsulated in the quantum crystals as shown in FIGS. 3(a) and 3(b). On the resultant brass substrate prepared by 3 minute agglomeration of the metal complex, 4,4'-bipyridine droplets (10 μL) of 10 mM, 1 μM and 100 nM were put down and the effect of surface plasmon enhancement were measured by using Raman Station 400 made in Parkin Elmer Japan Co. Ltd with a laser having a wavelength of 785 nm (resolution: 4.0 cm-1, laser output 300 mmW, spot size 100μΦ). Raman spectrum up to 100 nM can be confirmed as shown FIG. 1. Compared with SERS substrate prepared through CVD by Vladimir Poponin, Ph.D. wherein a Raman scattering spectrum of 100 μM can be detected, the present substrate can get a sensitivity of 1,000 times magnification. It can be thought that the sensitivity of 1000 times magnification was achieved because the quantum dots made of Ag nanocluster in the hexagonal plate-like crystal was formed on the brass substrate.

Example 2

Figure 4:
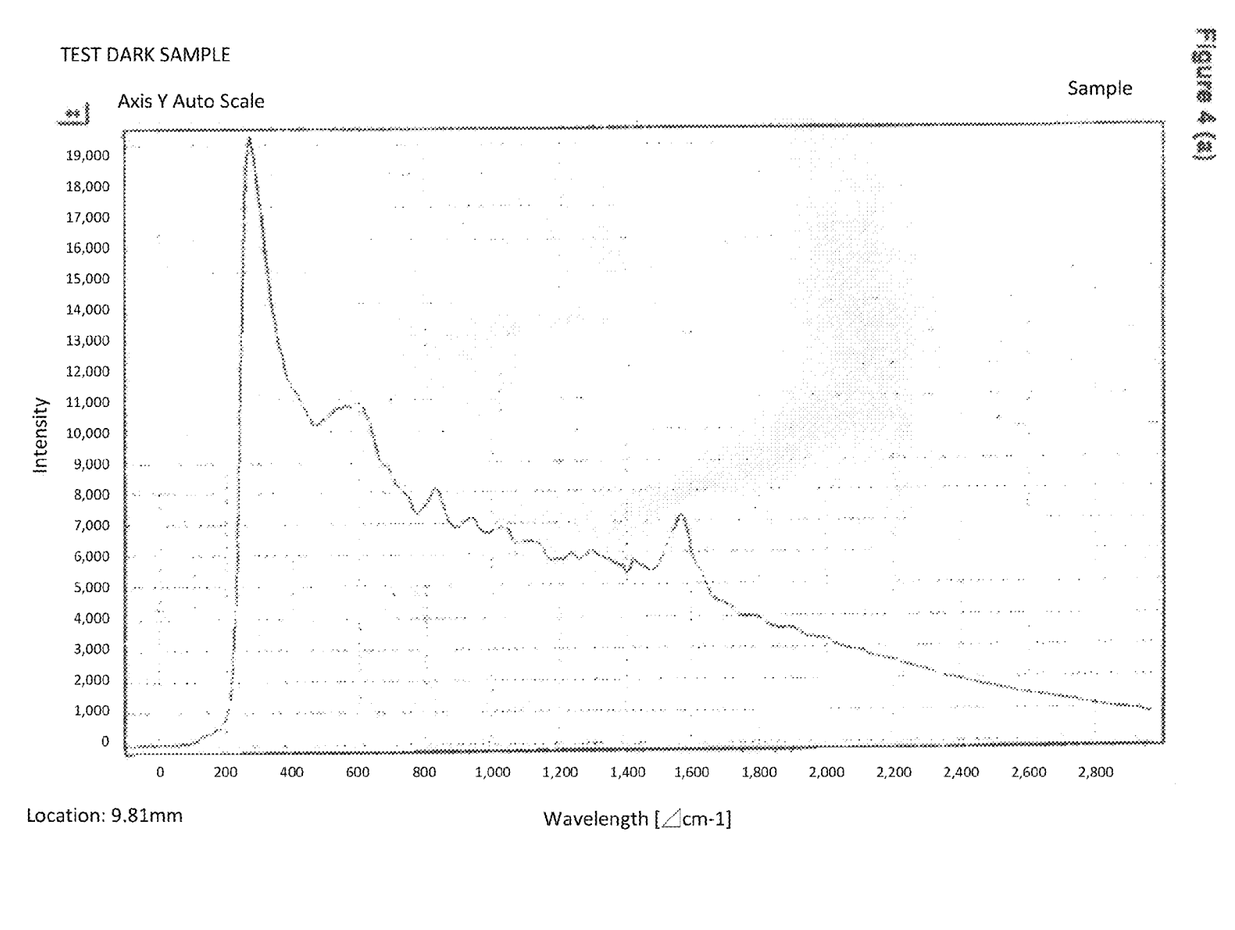
FIG. 4(a) is a graph showing a Raman scattering spectrum of pure water of 100 nM on a phosphor bronze substrate where Ag complex is formed in Ag nitrate aqueous solution according to the method of the present invention.
FIG. 4(b) is a graph showing a Raman scattering spectrum of 4,4'-bipyridine of 100 nM on a phosphor bronze substrate where Ag complex is formed in Ag nitrate aqueous solution according to the method of the present invention.

The Ag complex aqueous solution of 1,000 ppm (based on a weight of Ag atom) was prepared and one droplet of the aqueous solution was put on the phosphor bronze substrate and after 3 minutes, the droplet was blown off by Nitrogen gas to stop agglomeration of the metal complex. On each of the substrates, pure water or 4,4'-bipyridine of 100 nM were put and the effect of surface plasmon enhancement was measured by Raman spectroscopy made in Ramuda Vision Co. Ltd. with laser having a wavelength of 785 nm (Output: 80 mmW, Spot size: 50μΦ). The Raman spectrum can be confirmed up to 100 nM, as shown in FIGS. 4(a) and 4(b).

Example 3

In place of 4,4'-bipyridine, Rhodamine 6G (R6G) was used as a target sample to be detected. The aqueous solution of Ag thiosulfate complex was prepared and the phosphor bronze substrate was used. The R6G aqueous solution was put a drop on the metal complex substrate and the Raman spectrum of 1 μM can be confirmed by Raman spectroscopy (laser having a wavelength of 514 nm) made by Kaiser Co. Ltd as shown in FIG. 5. Compared with SERS substrate prepared through CVD by Vladimir Poponin Ph.D. wherein a Raman scattering spectrum of 100 μM can be detected, the present substrate can get a sensitivity of 1,000 times magnification.

Example 4

Humanized IgE monoclonal antibody (antibody concentration 1.23 mg/ml) (MIkuri Immuno Laboratory Co. Ltd. Lot. No. 214-01-002: Solution PBS: including 0.09% sodium azide) was diluted ten times with pure water and was mixed with Ag thiosulfate aqueous solution of 1,000 ppm (based on a weight of Ag atom) without amino acid at a mixture ratio of 1 to 1. The resultant solution was put as a drop on the phosphor bronze substrate in a same manner as Example 1 to prepare a measuring substrate for SERS.
After the confirmation that the Raman spectrum of the measuring substrate prepared by blending of the metal complex and the antibody was obtained by irradiation of the laser of the excitation wavelength 514 nm as shown FIG. 6 (a), an antigen was put a drop on the measuring substrate and was subjected to a Raman measuring to obtain the Raman spectrum, which was confirmed as shown FIG. 6 (b).
Compared with those Raman spectrum, it was confirmed that a peak was appeared near 1350 $cm^{-1}$ due to an antigen-antibody reaction, and as a result, the antigen-antibody reaction was detected when both were compared.

Comparative Example

In place of Ag complex solution used in Example 1, Ag nano colloid solution of 5,000 ppm (based on a weight of Ag atom) containing 2-pyrrolidone of 100 to 150 ppm as dispersant was used and other than that, a substrate was prepared in a same manner as Example 1. As Ag nanoclusters was much agglomerated as some solid-like points, there cannot be observed a surface plasmon resonance excitation effect.

INDUSTRIAL APPLICABILITY

By using the method of the present invention, the metal nanoclusters are precipitated at the same time as the metal complex crystals being precipitated from the aqueous solution, and therefore, the metal complex crystals, which encapsulate quantum dots in nano size or are precipitated on the surface, can be formed. The metal complex crystals, which prepared from the aqueous solution by using the method of the present invention, are probably the first case of nano sized complex crystals in the world. In case of Au, Ag, Cu or Pt, compared with nano dots produced by physical methods such as Vapor Deposition and the like, the quantum crystals of the present invention attain a thousand times magnification of surface plasmon resonance excitation effect, so that the quantum crystals are useful for surface plasmon resonance elements such as a SERS detecting substrate, a photoelectric transducer of solar-cells, a scanning near field optical microscopy element, and a metal needle for a medical thermotherapy.
In the above examples, although phosphor bronze and brass were used as a substrate metal, any other metal substrates are used corresponding to a kind of the metal of nanocluster. It is preferable that the substrate metal should be selected from a metal having a lower electrode potential than that of nanocluster. In case of silver nanocluster, copper and phosphor bronze substrate can be used in place of bronze. Though the metal carrier is usually in a form of a board-shaped, a particle-shaped, a needle-shaped and a capillary-shaped ones, any other forms can be used depending on the kind of use, wherein the metal complex crystals is deposited on this surface, and it is desirable to make it form the quantum crystal which encapsulates metal nano cluster.

What is claimed is:
1. A method of producing quantum crystals of a metal complex, the method comprising:
a step of providing an aqueous solution of a plasmon metal complex, wherein the plasmon metal complex is made of a ligand and a plasmon metal selected from the group consisting of Au, Ag, Cu, Ni, Zn, Al and Pt;

a step of contacting the aqueous solution of the plasmon metal complex with a carrier, wherein the carrier is made of a metal or a metal alloy that exhibits a natural electrode potential lower than a natural electrode potential of the plasmon metal or the carrier is made a metal that is adjusted to an electrode potential lower than an electrode potential of the plasmon metal; and a step of depositing the plasmon metal complex from the aqueous solution on the carrier to thereby form and arrange the quantum crystals of the plasmon metal complex on the carrier, wherein said formed and arranged quantum crystals have a plasmon enhancement effect.

2. The method of producing quantum crystals of a metal complex according to claim 1, wherein the carrier is one selected from the group consisting of a metal particle, a metal needle, and a metal film inside a capillary.

3. The method of producing quantum crystals of a metal complex according to claim 1, wherein the quantum crystals are quantum dots that are formed as nanoclusters of the plasmon metal complex on the carrier and are arranged at regular intervals on the carrier.

4. The method of producing quantum crystals of a metal complex according to claim 1, wherein the quantum crystals are formed as nanoclusters of the plasmon metal complex, wherein at least a part of the plasmon metal complex is in a state of ionic bonding with the ligand.

5. The method of producing quantum crystals of a metal complex according to claim 1, wherein the ligand is one selected from the group consisting of amino acid ion, ammonia ion, thiosulfate ion, and nitrate ion.

6. The method of producing quantum crystals of a metal complex according to claim 1, wherein the plasmon metal is one selected from the group consisting of Au, Ag, and Cu.

7. The method of producing quantum crystals of a metal complex according to claim 1, wherein the concentration of the plasmon metal in the aqueous solution is from 500 to 5,000 ppm.

8. The method of producing quantum crystals of a metal complex according to claim 1, wherein the concentration of the plasmon metal in the aqueous solution is from 500 to 2,000 ppm.

9. The method of producing quantum crystals of a metal complex according to claim 1, wherein the plasmon metal is Ag and the method further comprises:

a step of adding a dispersant into the aqueous solution, wherein the amount of the dispersant added is in a range of 1/5 to 1/150 of the atomic weight of the plasmon metal in the aqueous solution.

10. The method of producing quantum crystals of a metal complex according to claim 1, further comprising:

a step of adding an antibody into the aqueous solution of the plasmon metal complex, wherein the added antibody is deposited together with the plasmon metal complex on the carrier to thereby produce a device for detecting an antigen-antibody reaction.

* * * * *